US008787635B2

(12) United States Patent
Peng et al.

(10) Patent No.: US 8,787,635 B2
(45) Date of Patent: Jul. 22, 2014

(54) OPTIMIZATION OF MULTIPLE CANDIDATES IN MEDICAL DEVICE OR FEATURE TRACKING

(75) Inventors: Renbin Peng, San Jose, CA (US); Peng Wang, Princeton, NJ (US); Terrence Chen, Princeton, NJ (US); Dorin Comaniciu, Princeton Junction, NJ (US)

(73) Assignee: Siemens Aktiengesellschaft, Munich (DE)

( * ) Notice: Subject to any disclaimer, the term of this patent is extended or adjusted under 35 U.S.C. 154(b) by 349 days.

(21) Appl. No.: 13/097,497

(22) Filed: Apr. 29, 2011

(65) Prior Publication Data

US 2012/0004533 A1 Jan. 5, 2012

Related U.S. Application Data

(60) Provisional application No. 61/330,431, filed on May 3, 2010.

(51) Int. Cl.

| | |
|---|---|
| ***G06K 9/00*** | (2006.01) |
| ***A61B 6/00*** | (2006.01) |
| ***A61B 6/12*** | (2006.01) |
| ***A61B 8/12*** | (2006.01) |
| *A61B 19/00* | (2006.01) |

(52) U.S. Cl.

CPC ........... *A61B 8/12* (2013.01); *A61B 2019/5263* (2013.01); *A61B 6/5217* (2013.01); *A61B 6/12* (2013.01); *A61B 6/487* (2013.01); *A61B 6/504* (2013.01); *A61B 2019/5265* (2013.01)

USPC ............................ 382/128; 382/130; 382/131

(58) Field of Classification Search

USPC ................................................. 382/128, 131

See application file for complete search history.

(56) References Cited

U.S. PATENT DOCUMENTS

| | | | | |
|---|---|---|---|---|
| 7,289,652 | B2 * | 10/2007 | Florent et al. | 382/130 |
| 2007/0115364 | A1 * | 5/2007 | Kumaki | 348/208.99 |
| 2007/0260135 | A1 * | 11/2007 | Rousson et al. | 600/407 |
| 2007/0270692 | A1 | 11/2007 | Barbu et al. | |
| 2008/0095421 | A1 | 4/2008 | Sun et al. | |
| 2009/0062641 | A1 | 3/2009 | Barbu et al. | |
| 2009/0226040 | A1 | 9/2009 | Zhou et al. | |
| 2009/0292181 | A1 * | 11/2009 | Donaldson | 600/301 |
| 2009/0304251 | A1 | 12/2009 | Zheng et al. | |
| 2010/0067764 | A1 | 3/2010 | Lu et al. | |
| 2010/0119137 | A1 | 5/2010 | Schwing et al. | |
| 2010/0121181 | A1 | 5/2010 | Wang et al. | |
| 2010/0142787 | A1 | 6/2010 | Zheng et al. | |
| 2010/0254582 | A1 | 10/2010 | Liu et al. | |
| 2011/0064189 | A1 | 3/2011 | Wang et al. | |

* cited by examiner

*Primary Examiner* — Matthew Bella
*Assistant Examiner* — Weiwen Yang

(57) ABSTRACT

Multiple candidates are optimized in medical device or feature tracking. Possible locations of medical devices or features for each of a plurality of different times are received. The possible locations of devices are modeled using a probability function. An iterative solution to obtain the maximum of the probability function determines the possible locations to be used as the locations of the medical devices or features for each time. Where two or more medical devices or features are provided with a geometric relationship, such as being connected by a detected guide wire, the probability function may account for the geometric relationship, such as a geodesic distance between the possible locations for the two medical devices.

20 Claims, 4 Drawing Sheets

30 Receive Candidate Positions for Each Frame of a Sequence

32 Check Validity of Candidates

34 Remove Invalid Candidates

36 Identify Candidate for Each Frame based on Iteration of Probability Function

38 Determine Differences of Identified Candidates between Frames

40 Interpolate for Greater Distances

42 Output Candidate(s)

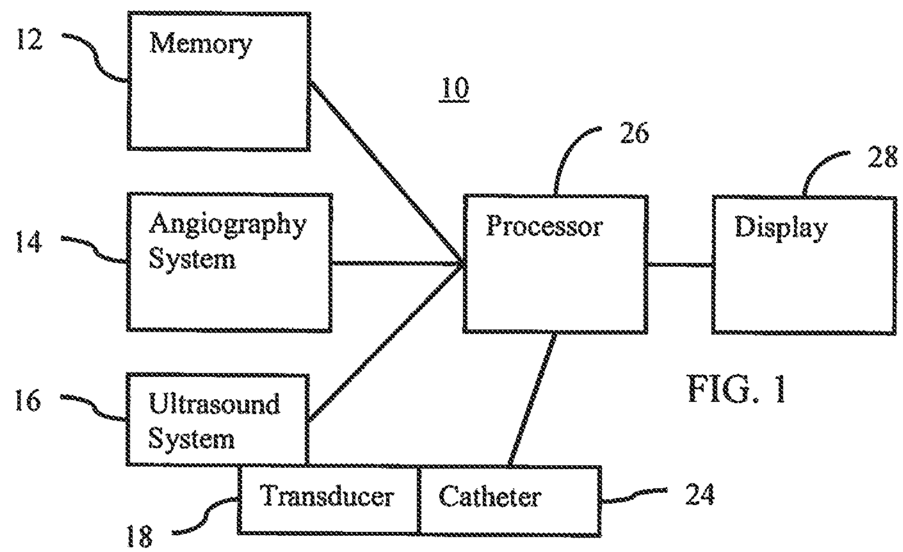
FIG. 1
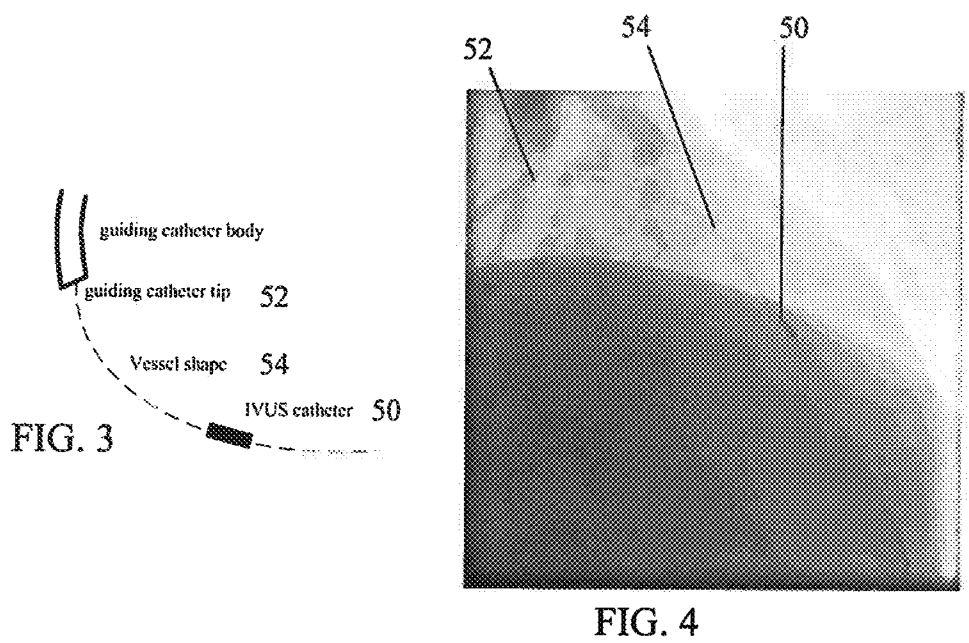
FIG. 3
FIG. 4

OPTIMIZATION OF MULTIPLE CANDIDATES IN MEDICAL DEVICE OR FEATURE TRACKING

RELATED APPLICATIONS

The present patent document claims the benefit of the filing date under 35 U.S.C. §119(e) of Provisional U.S. Patent Application Ser. No. 61/330,431, filed May 3, 2010, which is hereby incorporated by reference.

BACKGROUND

The present embodiments relate to identifying a location of a medical device or feature in an image.

The position of the catheter(s), other medical devices, or features may be determined in images. Such online tracking or position detection may be used in many applications, such as visual surveillance and real-time image guided interventions. However, due to complexity of the application environments, there is high possibility that the detection in the images may drift or be inaccurate due to missing detections, false alarms, occlusion, background noises, and other unpredictable factors.

2D X-ray fluoroscopy is routinely used for vascular interventions and for cardiac catheterization. Fluoroscopy is used for real-time monitoring of the procedure and catheter location visualization. However, 2D fluoroscopic images lack detailed anatomical information due to the incapability of X-ray in distinguishing among soft tissues. In order to augment the doctor's visualization of the body anatomy, for example, in the arterial fibrillation procedures, Intracardiac Echo (ICE) is used as an intra-operative modality to provide real-time cross-sectional ultrasound images.

In fluoroscopy, there are many types of devices of interest. For example, one is the guiding catheter, and another is the intravascular ultrasound (IVUS) catheter. In interventions, both the guiding catheter tip and IVUS catheter are undergoing breathing motions. In additional, the devices can be connected to each other. There can be motions between them. For example, the IVUS catheter is also being pulled back through a guiding catheter during the intervention. Precisely tracking both IVUS catheter and guiding catheter tips has important applications, such as in the co-registration of IVUS and angiography images. However, inaccuracies in detection of these devices may lead to inaccuracies in the applications.

BRIEF SUMMARY

By way of introduction, the preferred embodiments described below include methods, systems, instructions, and computer readable media for determining a first location of a first medical device or feature in imaging or optimizing multiple candidates in medical device or feature tracking. Possible locations of the medical device or feature for each of a plurality of different times are received. The possible locations are modeled using a probability function. An iterative solution to obtain the maximum of the probability function determines the possible location to be used as the location of the medical device or feature for each time. Where two or more medical devices or features are provided with a geometric relationship, such as being connected by a detected guide wire, the probability function may account for the geometric relationship, such as a geodesic distance between the possible locations for the two medical devices.

In a first aspect, a method is provided for determining a first location of a first medical device in imaging. A plurality of first candidate locations of a first medical device for each of a plurality of frames of medical data representing a patient is obtained. A plurality of second candidate locations of a second medical device for each of the plurality of the frames of the medical data is obtained. A processor identifies the first location of the first medical device in each of the frames. The first location is identified from the first candidate locations for the respective frame. The identification is solved iteratively as a function of a probability function. The probability function is a function of the location of first and second candidate locations, and distances between the first and second candidate locations. An indication of the first location is output for at least one of the frames.

In a second aspect, a non-transitory computer readable storage medium has stored therein data representing instructions executable by a programmed processor for optimizing multiple candidates in medical device or feature tracking. The storage medium includes instructions for receiving a plurality of detected positions of a medical device or feature for each of a plurality of image frames representing a patient, and selecting one of the detected positions in each of the image frames, the selecting iteratively solving, for each of the image frames, a probability function based on the detected positions in the image frame and a neighborhood of other image frames.

In a third aspect, a system is provided for optimizing multiple candidates in medical device tracking. A memory is operable to store data representing a region, at different times, of a patient and a catheter in the region. A processor is configured to calculate a location of the catheter in the region as represented by the data. The location is calculated by optimizing from a plurality of possible locations in the data at the different times in a Markov random chain. The optimizing uses iterated conditional modes to maximize posterior probabilities of the Markov random chain. A display is operable to display the location as calculated for each of the different times.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

FIG. 1 is a block diagram of one embodiment of a system for optimizing multiple candidates in medical device or feature tracking;

FIG. 3 is an example illustration of an ultrasound catheter and guiding catheter;

FIG. 4 is an example medical image showing an ultrasound catheter and guiding catheter;

DETAILED DESCRIPTION OF THE DRAWINGS AND PRESENTLY

Preferred Embodiments

Figure 2:
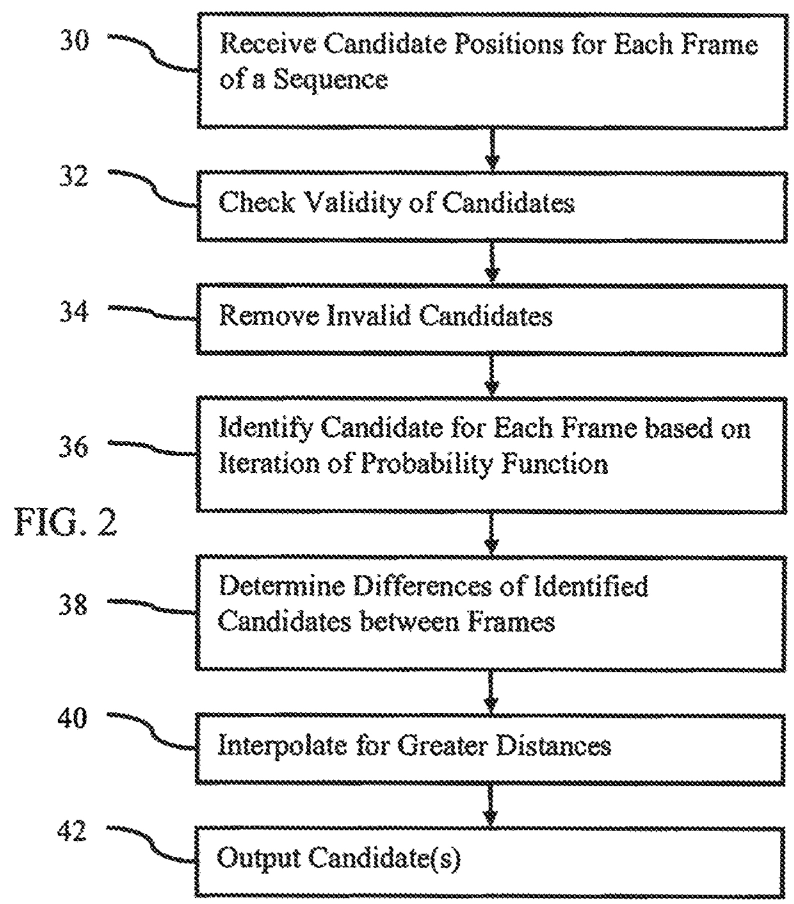
FIG. 2 is a flow chart diagram of one embodiment of a method for determining a first location of a first medical device or feature in imaging.

Accurate detection of a medical device in a medical image may be difficult. Rather than attempt to initially identify a single location in each given image, sets of possible locations in each of multiple images may be used to more accurately identify the single location in each given image. For example, online tracking results provide multiple candidates, from which the online tracking results are further refined. By using a plurality of possible locations in each frame (e.g., for each time) and a plurality of such frames (e.g., data for different times), more accurate detection may be provided. The sets of locations are combined or used together to correct errors from online tracking or detection. The best possible location is selected from multiple candidates obtained from online tracking.

The selection is treated as an optimization problem solved in a Markov random chain. Each tracking candidate is considered as one candidate state at a time stamp. All the states at different frames are organized in a Markov random chain. The temporal constraints between different frames and spatial constraints among different devices can be modeled in the Markov chain, in order to refine the online tracking results. Global constraints, such as from prior knowledge of particular applications, may be incorporated in the optimization.

Bayesian inference is used for optimization. An optimal set of states are sought by using iterated conditional modes (ICM) to maximize the posterior probabilities of the Markov random chain, therefore improving the online tracking results.

There may be different applications. In the example discussed below and shown in the Figures, online tracking results for the co-registration of intravascular ultrasound (IVUS) and angiography data is provided. The location of the catheters or other medical device in the angiography data is identified. These locations may be used to determine a spatial location of the scan plane of the ultrasound catheter relative to the patient or the angiogram. Other applications include any catheter, stent, or other procedure where the location of medical devices in medical imaging is to be identified by a computer. For example, a guide wire, a needle, or a pigtail catheter are tracked together with a guiding catheter in image guided interventions.

FIG. 1 shows a system 10 for optimizing multiple candidates in medical device tracking. The system 10 includes a memory 12, an angiography system 14, an ultrasound system 16, a catheter 24, a transducer 18, a processor 26, and a display 28. Additional, different, or fewer components may be provided. For example, a network or network connection is provided, such as for networking with a medical imaging network or data archival system. As another example, a preoperative imaging system, such as a computed tomography or magnetic resonance imaging system, is provided with or as an alternative to the memory 12. In another example, a user interface is provided.

The processor 26 and display 28 are part of a medical imaging system, such as the diagnostic or therapy ultrasound system 16, angiography system 14, x-ray, computed tomography, magnetic resonance, positron emission, or other system. Alternatively, the processor 26 and display 28 are part of an archival and/or image processing system, such as associated with a medical records database workstation or server. In other embodiments, the processor 26 and display 28 are a personal computer, such as desktop or laptop, a workstation, a server, a network, or combinations thereof. The processor 26, display 28, and memory 12 may be provided without other components for implementing the method.

The memory 12 is a graphics processing memory, a video random access memory, a random access memory, system memory, random access memory, cache memory, hard drive, optical media, magnetic media, flash drive, buffer, database, combinations thereof, or other now known or later developed memory device for storing data or video information. The memory 12 is part of an imaging system, part of a computer associated with the processor 26, part of a database, part of another system, a picture archival memory, or a standalone device.

The memory 12 stores data representing a region, at different times, of a patient. The data includes information representing the catheter 24 while in the region. The catheter may be difficult to recognize relative to other structures in the region. The region is a two or three-dimensional region. The region is of any part of the patient, such as a region within the chest, abdomen, leg, head, arm, or combinations thereof.

The data is from scanning the region by any medical imaging modality. Any type of data may be used, such as medical image data (e.g., ultrasound, x-ray, computed tomography (CT), magnetic resonance imaging (MRI), or positron emission tomography). In one embodiment, the data representing the patient volume is computed tomography data, x-ray data, angiography data, fluoroscopy data, magnetic resonance data, or combinations thereof. The data represents the patient prior to or during treatment. For example, angiography or fluoroscopy data is acquired during a catheterization. As another example, CT or MRI data is acquired prior to intervention, such as just prior to (same day) or during a previous appointment on a different day.

As an alternative to storing image data, the memory 12 stores just candidate locations for the position of the catheter 24 or other medical device. The image data is not stored or, even if stored, not further used. The location of the medical device or devices is determined from candidate locations without additional image context other than used in the initial detections.

The memory 12 or other memory is alternatively or additionally a computer readable storage medium storing data representing instructions executable by the programmed processor 26 for optimizing multiple candidates in medical device or feature tracking. The instructions for implementing the processes, methods and/or techniques discussed herein are provided on non-transitory computer-readable storage media or memories, such as a cache, buffer, RAM, removable media, hard drive or other computer readable storage media. Non-transitory computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The x-ray angiography system 14 is any now known or later developed angiography system. For example, the angiography system 14 includes an x-ray source and an x-ray detector on a C-arm or other robotic mechanism for positioning relative to the patient. The angiography system 14 includes position sensors for determining changes in position of the x-ray source and/or detector. In alternative embodiments, the angiography system 14 is a CT angiography or MR angiography system.

For angiography imaging, a contrast agent (e.g., iodine) may be injected into a patient. The contrast agent provides a detectable response to x-rays. By flowing through the circulatory system, the contrast agent may provide detectable response highlighting the circulatory system, such as the vessels, veins, and/or heart. Alternatively, no contrast agent is injected for fluoroscopic imaging. By transmitting x-rays through the patient to the detector, a projection image is provided. Any tissue, bone, catheter, and contrast agent along the path of travel of the x-ray beam interacts with the x-rays, causing a detectable difference in intensity at the detector. Since each pixel or location of the detector represents an accumulation of responses along the path of travel, the fluoroscopic image is a projection image of the region.

An angiographic image may be generated with or without response from the catheter 24. For example, the catheter 24 is positioned in the x-ray beam adjacent to but outside the patient. Such positioning may be used for an initial registration with an ultrasound system. An angiographic image is generated with response from the catheter. During intervention, the catheter may be positioned within the patient. One or more angiographic images are generated in real-time or during the interventional procedure.

The x-ray beam of the angiography system 14 may pass through or intersect the patient volume. For example, the catheter 24 is to be used for ablation of heart wall tissue, for ultrasound scanning to assist in stent placement, or for other imaging of the heart or circulatory system. The patient volume includes at least a portion of the heart. The x-ray beam is positioned to also project through the heart.

The ultrasound system 16 is any now known or later developed ultrasound imaging system. For example, the ultrasound system 16 includes the transducer 18 for converting between acoustic and electrical energies. Transmit and receive beamformers relatively delay and apodize signals for different elements of the transducer 18. B-mode, Doppler, or other detection is performed on the beamformed signals. A scan converter, memory, three-dimensional imaging processor, and/or other components may be provided.

The transducer 18 is a one-, two-, or multi-dimensional array of piezoelectric or capacitive membrane elements. For example, the transducer 18 is a one-dimensional array of elements within or on the intravascular ultrasound catheter 24 used for intervention or a different catheter. In another embodiment, the transducer 18 is part of a probe for use within the patient, such as a transesophageal probe.

The catheter 24 is any now known or later developed catheter for intervention or other use within a patient. The catheter 24 is sized and shaped for use in the circulatory system, such as having a diameter of 10 French or less, but a length of a foot or more. The catheter 24 is adapted for insertion within the patient, such as through a vessel or vein for extending into a heart chamber. The catheter 24 may include guide wires or be inserted through another previously positioned guide catheter. The catheter 24 may include an electrode, scalpel, balloon, stent, or other device for treatment of the heart or circulatory system.

The processor 26 is a general processor, central processing unit, control processor, graphics processor, digital signal processor, three-dimensional rendering processor, image processor, application specific integrated circuit, field programmable gate array, digital circuit, analog circuit, combinations thereof, or other now known or later developed device for determining position or iterative solving. The processor 26 is a single device or multiple devices operating in serial, parallel, or separately. The processor 26 may be a main processor of a computer, such as a laptop or desktop computer, or may be a processor for handling some tasks in a larger system, such as in an imaging system. The processor 26 is configured by instructions, design, hardware, and/or software to be able to perform the acts discussed herein, such as iterative solution of a probability function to select a location from a group of candidates.

The processor 26 determines a catheter position relative to the patient region or within an image. The position may be determined for registration of images and/or for assisting medical professionals by display of the image with the catheter highlighted. The processor 26 is configured to calculate a location of the catheter 24 in the region as represented by the data. The location is a point, line, area, volume or surface location. For example, the location is a center of a transducer, center of an end of a guide catheter, a tip, or other point on a catheter.

The data includes multiple frames of data. Each frame of data represents the region at a time. The data is at any stage of processing, such as data prior to or after detection and/or conversion to a display format. The frame of data may be image data prior to any display or after display. The frame of data is from the medical scan or is locations identified from a medical scan. For example, the data is candidate locations detected by the processor 26 or another device. The candidate locations are a plurality of possible locations for the medical device, one of which is likely the actual location of the medical device as represented in the scan data. The processor 26 may detect the candidate locations from scan data prior to iterative solution to select specific locations or may receive the locations as the frame from an output of a detector.

The processor 26, using candidate locations of the catheter, optimizes from a plurality of possible locations. FIG. 2 shows an example flow chart associated with the calculating. Multiple locations for each of different times are used in a Markov random chain to calculate which of the candidate locations for each time is to be used. Iterated conditional modes are used maximize posterior probabilities of the Markov random chain.

Using an angiography example, the processor 26 locates two devices, the IVUS catheter and a catheter guide tip. Given a detected guide wire between the two devices, the spatial relationship of the devices may be used in the probability function for the solution. The posterior probabilities are a function of the possible locations of the IVUS catheter, possible locations of a catheter guide, and a geodesic distance between them. By an iterative solution solving for maximum of the probability function, the processor 26 calculates the locations of the devices.

The display 28 is a monitor, LCD, projector, plasma display, CRT, printer, or other now known or later developed devise for outputting visual information. The display 28 receives images, graphics, or other information from the processor 26, memory 12, angiography system 14, or ultrasound system 16.

One or more images representing a catheter position relative to a patient region are displayed. The image may be of a location, such as displaying coordinates. The image may be of a medical scan representing the region of the patient. The location of the medical device is highlighted, marked by a graphic, or otherwise indicated on the image. For example, an image includes fluoroscopic information showing the location of a catheter. Where a sequence of images is displayed, the location of each medical device is indicated in each of the images.

The location in one or more images may be used for purposes other than display. For example, the location is used to register a position of an ultrasound scan plane relative to a volume of an angiogram or other medical scan data.

Other images may be displayed, such as a rendering from a three-dimensional ultrasound data set or a two-dimensional ultrasound scan. The fluoroscopic image may be displayed separately. Any of the types of data may be combined to form an image or displayed separately at a substantially same time. For example, preoperative and fluoroscopic images are displayed separately with or without a separate ultrasound image. As another example, preoperative and fluoroscopic images are displayed separately with an image formed from a combination of the preoperative and fluoroscopic images or data.

FIG. 2 shows a method for determining a first location of a first medical device in imaging. The method is implemented by the system 10 of FIG. 1 or another system. The acts are performed in the order shown or other orders. Additional, different, or fewer acts may be provided. For example, the output act 42 is not provided, but instead the selected locations for the sequence are used to register medical scans. As another example, acts 32 and 34 are not provided. In another example, acts 38 and 40 are not provided.

In act 30, a plurality of detected positions of a medical device is obtained. The detected positions are obtained by loading from memory or transfer from a network or other device. In other embodiments, the detected positions are obtained by image processing, such as applying one or more detectors. The images to be processed or the images from which the locations are detected may or may not be received. Any type of image data may be used, such as angiography or fluoroscopic images. Any technique for obtaining by detecting or obtaining by receiving the output of detection may be used.

Multiple detected positions are received for each of a plurality of image frames representing a patient. The detected positions are candidate locations for one or more medical devices. The detected positions may or may not be the actual location.

FIG. 3 shows the example arrangement of an IVUS catheter 50, guide catheter 52, and a guide wire 54 connecting the IVUS catheter 50 to the guide catheter 52. The guide wire 54 extends within the IVUS catheter 50, so the IVUS catheter 50 being detected is the tip of the catheter or center of a transducer. Other parts may be detected. In this example, the end or center of the end of the guide catheter 52 is also sought.

FIG. 4 shows a similar arrangement as FIG. 3, but in a fluoroscopic image. The tip or transducer of the IVUS catheter 50 may or may not stand out, and may be confused with other structures in the region, including the guide wire 54. The end of the guide catheter 52 stands out even less and may be confused with other structure in the region. Automated or computer assisted detection may identify multiple possible locations for the devices 50, 52 in each given image, so a plurality of candidate locations of each medical device for each of a plurality of frames of medical data representing a patient are obtained.

In each video frame or frame of data, multiple detection and tracking results for the guiding catheter tip 52, catheter body and/or IVUS catheter 50 are received. Any now known or later developed detection may have been used to provide the candidate locations. In one example, learning-based detectors are used for object detection and tracking. The learning-based classifier is trained from a set of off-line collected data, including both object samples (positive) and non-object samples (negative), to learn the decision boundary that separates the positive from negative samples. Learning based detection adapts for different detection tasks, such as learning to detect different types of devices. One example learning-based classifier is the probabilistic boosting tree (PBT). PBT is a tree-based generalization of AdaBoost classifiers for modeling a complex distribution of a class of objects. The classifiers are trained from any one or more types of features, such as using Haar features. The detectors may be constructed in a hierarchical way. First, a position detector is trained to locate the position of objects. An orientation detector is then trained at images rotated at different angles to detect devices at arbitrary orientations. Furthermore, a size detector is applied to search across different scales by varying the size of Haar features. Each detection candidate for each medical device is associated with a confidence score that is provided by PBT. In one example, four types of detectors are trained for the device tracking. The four types of detectors are for the IVUS transducer, the guiding catheter body, the guiding catheter tip, and the wire body, respectively. Filtering, other selection, other classifiers, or other processes may be used to detect candidates for one or more of the medical devices.

Due to image artifacts and low visibility of devices, there may be false detections of devices. To make the tracking robust to detection errors, the true tip and catheter positions are inferred by taking into account all the available detection and tracking results, and their co-relationship in the spatial and temporal domains.

In an alternative embodiment to a programmed or machine-trained classifier, the user indicates possible candidates. Alternatively, the user assists in catheter or other device identification. Other landmarks instead of or in addition to the catheter may be used. A plurality of landmarks may be obtained offline. Using the catheter may allow for less overlap of the fluoroscopic region with the ultrasound scanned volume.

The same or different detector is applied for different medical devices where there are multiple devices being tracked or detected. Candidate locations for each of the devices in each of the frames are obtained. In the examples of FIGS. 3 and 4, there are multiple guiding catheter tip candidates from which one is to be selected as the inferred position.

Other information or detections may be received. For example, the location of the guide wire is detected. The guide wire may be indicated by the user (e.g., tracing) in one frame and tracked to determine the location in other frames. Alternatively, the guide wire is detected by filtering to enhance linear, curve, or line structures. Gradient-based, pattern matching, region growing or other detection is used to determine the location of the guide wire in each frame. Alternatively or additionally, the motion of the guide wire is determined. The change in the position in the guide wire is determined. The guide wire is treated as having a constant curve, so one motion vector of translation and rotation of the guide wire may be employed as input data. In other embodiments, the motion includes one or more factors for change in curve or bend.

The number of the input candidates may be pruned by checking validity in act 32. Tens, hundreds or other number of frames of data are received. Each frame may have one or more (e.g., tens or hundreds) of candidate coordinates. To increase efficiency and/or to reduce the opportunity for incorrect selection, the number of candidates may be limited. For example, the most likely ten or twenty candidates are used. The best candidates are determined from the detector or using other criteria.

As another example, a criterion may be applied to prune the number of candidates based on the criterion rather than limiting to a certain number of candidates. For example, validity of the candidates is checked based on a nearest neighbor approach. The best candidates output by the detection are selected. Other candidates within a neighborhood radius are selected. The remaining candidates are considered outliers and not used.

The validity of the candidate locations is checked for each of the frames. A reference location is selected, such as the detected guide wire. The location of each candidate relative to the reference is used as a validity check. Spatial, temporal, or both spatial and temporal criteria may be used. One or multiple criteria may be applied.

In one embodiment for IVUS catheter candidates, the guide wire is represented as a spline. If the coordinates of a detected candidate for the IVUS catheter is considered as an outlier of the guide wire, the candidate is labeled as invalid detection. Any distance may be used to define an outlier, such as requiring a position on the guide wire or within 1, 2, or other number of millimeters.

In one embodiment for a guiding catheter candidates, the criteria compares between frames. The geodesic distance between each candidate and a reference location is determined. The reference location may be IVUS catheter location on the guide wire, a user selected location on the guide wire, or other location on the guide wire. For each frame, a location of each candidate is also interpolated from the corresponding candidates in other frames. The geodesic distance for the interpolated location is calculated. A candidate location of a guiding catheter tip is considered to be invalid if the difference between the candidate location geodesic distance from the reference and the interpolated geodesic distance from the reference is larger than a preset threshold. Other approaches to identify candidates that move more than the guide wire may be used. Approaches relying on other spatial or temporal criteria may be used.

In act 34, candidate locations that are invalid are removed. The candidates are no longer considered candidates and are not used to select the final location. Any candidate location failing the criteria is removed. Alternatively, the candidates most severely failing the criteria are removed, resulting in a given number of candidates for each frame.

Figure 5:
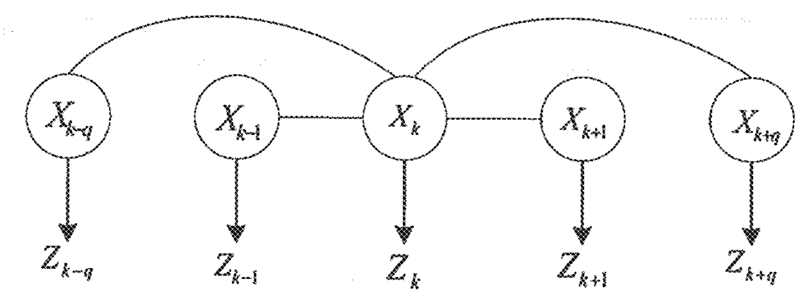
FIG. 5 is an example graphical model of a Markov chain representing locations of a medical device.

If all of the candidates for the guiding catheter tip and/or IVUS catheter are invalid, the frame may not be used. Where all candidates are likely far from the true positions, a large error may be introduced if these detections are involved in the inference procedure. The frame is considered at a "none-state" if all of the detection results are invalid. If all the candidates of the guide tip or catheter in a frame are labeled as none-state, the Markov chain in FIG. 5 is broken, and the candidate information included in the none-state frame is not employed for the inference of other frames.

In act 36, a processor identifies one location of the medical device in each of the frames. The location is identified from among the candidate locations for the respective frame. Rather than determine a new location, one of the candidate locations is selected as the detected position of the device. Such selection occurs in each of the frames. More than one candidate may be selected. The selection is performed for each of the medical devices.

One or more parameters are used for identification. In one embodiment, the identification for a frame is based on the candidate locations in the given frame and candidate locations in other frames. The identification is also based on the motion of the guide wire. Alternatively, just the candidate locations without guide wire motion are used. Other inputs may be used.

The location for each medical device is identified based in part on the candidate locations for that medical device and one or more other medical devices. Alternatively, the identification for one medical device is performed independently of the location of other medical devices.

The identification is performed by inferring the maximum of a probability function. The inference problem is formulated as an optimization problem. The candidate locations from all, a windowed subset, or other collection of multiple frames are used to optimize the probability of each candidate. The candidate with the optimum location is identified.

Figure 6:
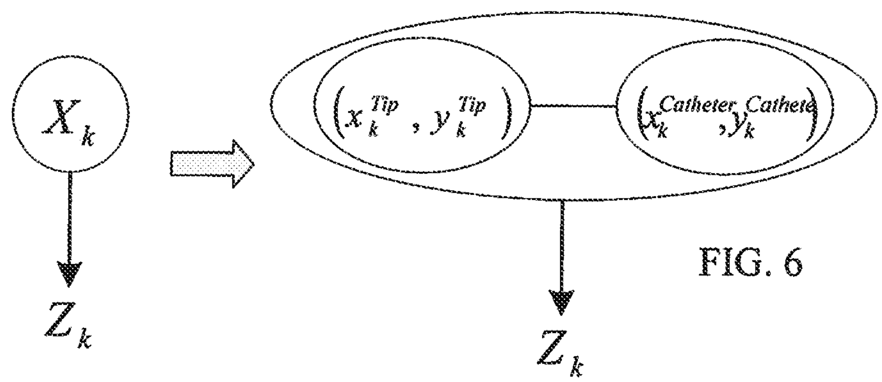
FIG. 6 is a graphical representation of ultrasound and guide catheter locations for one of the frames in the example of FIG. 5.

In one embodiment, a graphical model is constructed and the maximum a posterior probability (MAP) approach is employed to find the inference results. FIG. 5 shows an example graphical model. In the figure, $X_k$ denotes the actual or true positions of guiding catheter tip and IVUS catheter in the $k^{th}$ frame: $X_k=\{(x_k^{Tip},y_k^{Tip}),(x_k^{Catheter},y_k^{Catheter})\}$. The true or actual position is shown clearly in FIG. 6. $Z_k$ represent the observations in the $k^{th}$ frame, which include the detection results of guide tip, catheter, and the motion of guide wire: $Z_k=\{(\hat{x}_{k,j}^{Tip},\hat{y}_{k,i}^{Tip}),(\hat{T}_{x:k,j}^{Guidewire},\hat{T}_{y:k,j}^{Guidewire},\hat{\theta}_{y:k,j}^{Guidewire}),(\hat{x}_{k,l}^{Catheter},\hat{y}_{k,l}^{Catheter})\}$. $(\hat{x}_{k,i}^{Tip},\hat{y}_{k,i}^{Tip})$ denotes the $i^{th}$ detected positions of guiding catheter tip, i=1, 2, . . . , $N_k^{Tip}$, and $N_k^{Tip}$ is the total number of tip detections in the frame. $(\hat{T}_{x:k,j}^{Guidewire},\hat{T}_{y:k,j}^{Guidewire},\hat{\theta}_{y:k,j}^{Guidewire})$ are the motion parameters of the guide wire. In this example, the motion parameters are the translations in horizontal and vertical directions as well as the rotation angle. The notations for the detection results of guide wire and IVUS catheter in FIGS. 5 and 6 are similar to guide tip.

Given the number of variables and corresponding multiple combinations of different candidates, the maximization of the probability function is iteratively solved for each of the image frames. The identification is an iterative solution of the probability function. Any probability function may be used. For example, a Gaussian distribution of probabilities is assumed. Other distributions may be used. Applying the Gaussian distribution, the posterior probabilities of a Markov random chain are iteratively maximized. The Markov random chain is of the candidate locations in a sequence of the frames. For two or more devices, the multi-candidate inference problem is modeled under the Bayesian framework based on the graphical model of FIG. 5. In one example, the probability function may be represented as:

$$P(X \mid Z) \propto P(Z \mid X)P(X) = \left(P(Z_0)\prod_{k=1} P(Z_k \mid X, Z_{k-1}, \ldots , Z_0)\right)\left(P(X_0)\prod_{k=1} P(X_k \mid X_{k-1}, \ldots , X_0)\right) \approx \left(P(Z_0)\prod_{k=1} P(Z_k \mid X_k)\right) \left(P(X_0)\prod_{k=1} P(X_k \mid X_{k-q}, \ldots , X_{k-1}, X_{k+1}, \ldots , X_{k+q})\right)$$

where $X=\{X_0, \ldots, X_k, \ldots\}$, $Z=\{Z_0, \ldots, Z_k, \ldots\}$. (2q+1) is a size of the neighborhood and q is a non-negative integer. The neighborhood is a temporal neighborhood of frames. For example, q=1 provides 3 frames in the neighborhood, the frame k for which the candidate is selected, the previous frame k−1, and the subsequent frame k+1. Non-symmetric windows for the neighborhood may be used. The inference for each given frame is based on the information provided by the neighboring frames as well as the observations included in the given frame. The first part of the probability function is based on the candidates in the given frame, and the second part of the probability function is based on the candidates in different frames.

The probability function is for a single-candidate or multi-candidate inference. In the IVUS catheter and guide catheter example of FIG. 3, multiple-candidate inference is used. The probability or likelihood model is defined relative to the particular problem. Since the candidates form the neighborhood of each detection result, including the actual or true results themselves, the Gaussian model is assigned to the candidates. In addition, the geodesic distance between the guiding catheter tip and IVUS catheter along the guide wire is assumed to change smoothly as the inference iteration proceeds.

To optimize the probability function for the given frame, the probabilistic model is defined in terms of the available information, such as the sets of candidates for the different devices. In one embodiment, the probability function includes differences between an inferred location and the candidate location nearest to the inferred location for one device, includes differences between an inferred location and the candidate locations nearest to the inferred location for the other device, and includes the distances between the candidate locations of the different devices. An example is represented as:

$$P(Z_k \mid X_k) \propto \exp\left\{\begin{array}{l} -W_{Likelihood-1}\dfrac{\left(\left(x_k^{Tip}-z_{x:k}^{\prime Tip}\right)^2+\left(y_k^{Tip}-z_{y:k}^{\prime Tip}\right)^2\right)}{2\sigma^2_{Likelihood-1}} \\ -W_{Likelihood-2}\dfrac{\left((x_k^{Catheter}-z_{x:k}^{\prime Catheter})^2+(x_k^{Catheter}-z_{x:k}^{\prime Catheter})^2\right)}{2\sigma^2_{Likelihood-2}} \\ -W_{Likelihood-3}\dfrac{\left(d_k^{Tip-Catheter}-d_k^{\prime Tip-Catheter}\right)^2}{2\sigma^2_{Likelihood-3}} \end{array}\right\}$$

where $(z'^{Tip}_{x:k}, z'^{Tip}_{y:k})$ and $(z'^{Catheter}_{x:k}, z'^{Catheter}_{y:k})$ are the positions of the candidate coordinates of the guide catheter tip and IVUS catheter which are the nearest neighbors of the inferred or true positions $(x_k^{Tip}, y_k^{Tip})$ and $(c_k^{Catheter}, y_k^{Catheter})$, respectively. The inferred positions are the currently identified or selected positions sought by the iterative solution of this probability function. $d_k^{Tip\text{-}Catheter}$ and $d'^{Tip\text{-}Catheter}_k$ are the geodesic distances between the candidate locations for the tip and catheter in the $k^{th}$ frame, along the guide wire, of the inferred positions in the current and previous iterations, respectively. W and $\sigma^2$ are weight and variance.

$d_k^{Tip\text{-}Catheter}$ and $d'^{Tip\text{-}Catheter}_k$ use the relative position of the different devices as part of the probability function. Since the devices are spatially related by the possibly curving guide wire, the geodesic distance along the curve of the guide wire is used. The spline representation of the guide wire provides the curve for distance calculation. During the derivation of the geodesic distance given the positions of tip and catheter inferred in a current iteration, the relation between the Euclidean distance and geodesic distance along the guide wire is employed. For example, the distances between the current inferred location x and the candidate are Euclidean distances while the geodesic distance is used between the inferred locations x of the different devices. The distances are represented in the probability function as differences. The geodesic distance of each frame is updated using the latest inferred tip and catheter positions.

The prior term or portion of the probability function relating the candidates over time is defined as well. The position is identified with the probability function including probabilities for a first one of the frames and probabilities for one or more others of the frames. Given the iterative solution, the probabilities for the other frames may include the predicted or currently inferred locations in the other frames. The true position of the guide tip and catheter in the current frame is assumed, and those candidates projected from the neighboring frames obey the Gaussian model. The state model is a linear Gaussian. Additionally, the geodesic distances of the neighboring frames are also assumed to obey a Gaussian smoothness assumption. For simplicity, only the successive three frame case is used below, but a greater q value may be used. For the three frame case, the prior probability function is represented as:

$$P(X_k \mid X_{k-1}, X_{k+1}) \propto \exp\left\{ \begin{array}{l} -W_{Prior-1} \dfrac{\left(\left(x_k^{Tip} - \partial x'^{Tip}_{k-1} - \beta x'^{Tip}_{k+1}\right)^2 + \left(y_k^{Tip} - \partial y'^{Tip}_{k-1} - \beta y'^{Tip}_{k+1}\right)^2\right)}{2\sigma^2_{Prior-1}} \\ -W_{Prior-2} \dfrac{\left((x_k^{Catheter} - \partial x'^{Catheter}_{k-1} - \beta x'^{Catheter}_{k+1})^2 + (y_k^{Catheter} - \partial y'^{Catheter}_{k-1} - \beta y'^{Catheter}_{k+1})^2\right)}{2\sigma^2_{Prior-2}} \\ -W_{Prior-3} \dfrac{\left(d_k^{Tip-Catheter} - \partial\left(d_{k-1}^{Tip-Catheter} - d_{Pullingback}^{k-1}\right) - \beta\left(d_{k+1}^{Tip-Catheter} + d_{Pullingback}^{k+1}\right)\right)^2}{2\sigma^2_{Prior-3}} \end{array} \right\}$$

where $(x'^{Tip}_{k-1}, y'^{Tip}_{k-1})((x'^{Catheter}_{k-1}, y'^{Catheter}_{k-1}))$ and $(x'^{Tip}_{k+1}, y'^{Tip}_{k+1})\ ((x'^{Catheter}_{k+1}, y'^{Catheter}_{k+1}))$ are the positions of the tip (catheter) predicted from the previous (e.g., $(k-1)^{th}$) and next (e.g., $(k+1)^{th}$) frames to the $k^{th}$ frame, respectively. $d_{Pulling\text{-}back}^{k}$ is the geodesic distance in the $k^{th}$ frame. $\partial$ and $\beta$ are smoothing coefficients. For each iteration, the frame and prior terms are multiplied in the probability function example shown above. The iteration seeks to maximize the result of the multiplication.

In an example implementation, $W_{Likelihood-1} = W_{Prior-1} = 0.3$, $W_{Likelihood-2} = W_{Prior-2} = 0$, $W_{Likelihood-3} = W_{Prior-3} = 0.7$, $\sigma_{Likelihood-1}^2 = 200$, $\sigma_{Likelihood-2}^2 = 200$, $\sigma_{Likelihood-3} = 400$, $\sigma_{Prior-1}^2 = 800$, $\sigma_{Prior-2}^2 = 800$, and $\sigma_{Prior-3}^2 = 150$, $\partial = \beta = 0.5$. The threshold for judging the none-state status of the guide catheter tip is 5 (e.g., the geodesic difference is 5). The maximum number of IVUS catheter tip candidates is set to be 20. Other values may be used. The values may be learned by experimentation and/or machine optimization.

Figure 7:
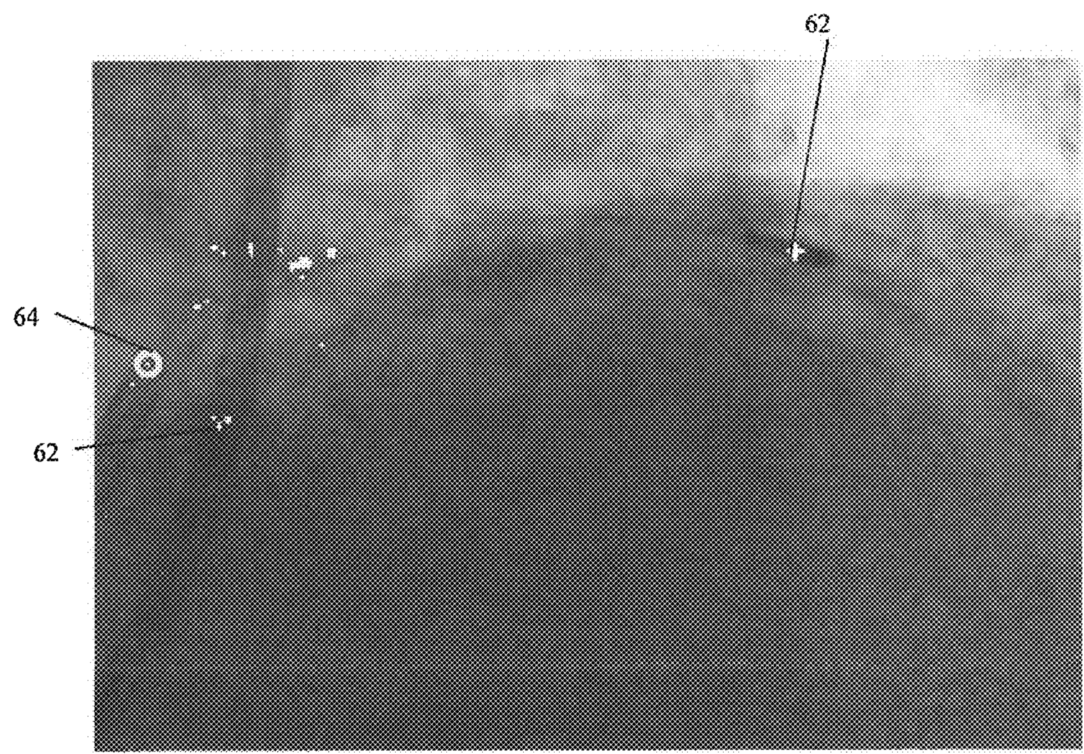
FIG. 7 is an example image showing candidate locations and an actual location of a guide catheter.

FIG. 7 shows inference results for a catheter guide tip. The small crosses represent candidate locations. There are two general regions (e.g., see crosses in the group 62 for one region of candidates) where the candidate locations are not near the true location 64. Using the iterative solution of the probability function, the best candidate 64 is selected. The best candidate is closest or at the true tip position. FIG. 7 shows one location for the IVUS catheter to limit confusion in the drawing. This one location is used as a candidate set of one position in the probability function to identify the guide tip. In alternative embodiments, a plurality of candidates for the IVUS catheter is also provided.

The iterative solution is performed for each frame. A candidate location is selected or an inferred location is identified for each frame. The location for each frame may be solved at a same time as the other frames. For example, each iteration refines the locations in the frames. Alternatively, the location in each frame is sequentially solved through multiple iterations.

Differences between the locations in the different frames may be used to check for errors. Referring to FIG. 2, the differences between the identified locations are determined in act 38. The sequence of images is of the same region such that frame-to-frame differences represent a detection change rather than patient or imaging system motion. Alternatively, the frames are spatially aligned by correlation of the data, measurements by sensors, or user input prior to difference determination. After alignment, differences beyond a threshold amount are identified.

In another embodiment, the translation and rotation of the guide wire is used to remove motion. The positions of the inferred guide tip from the previous and next frame or between a group of frames are projected to the current frame using an affine transformation. The parameters of the affine transformation are translation and rotation of the guide wire. The translation and rotation of the identified locations of the devices are considered to be the same as the guide wire. Any difference from guide wire motion beyond a threshold may be the result of inaccurate detection.

The geodesic distance may be used to correct for motion. The geodesic distance changes over time should be smooth. Linear interpolation is employed in act 40 during a geodesic distance update. For each iteration, the geodesic distance is checked. If the distance is outside a range (e.g., beyond low or high thresholds), the geodesic distance for the given frame and iteration is replaced by an interpolated or filtered distance. For example, the locations from different frames are interpolated over time to the current frame. Any number of frames may be used for the interpolation. For example, 31 frames with the current frame at the center are used to interpolate a distance in the current frame.

In act 42, an indication of the one or more locations is output for at least one of the frames. The indication is the coordinates. For registering images, the coordinates may be used to determine spatial relationship without displaying the coordinates. A position of the ultrasound image plane relative to the angiogram or other image is displayed. In other embodiments, the image is output with the location indicated on the image. A marker or other highlighting in an image is provided to the user. The actual coordinates may be provided to the user.

In alternative embodiments, the candidates are for detected features of a patient, such as a physiological structure, instead of or in addition to medical devices.

In another alternative embodiment, a location of a feature or device is known or assumed to be more robust than others and used for iteratively solving to identify the location from a set of candidates for another feature or device. For example, there is one input IVUS catheter candidate with highest confidence score, which is considered as the inferred position. The original detection accuracy of the IVUS catheter may be high, and the none-state judgment result may be reliable. The input IVUS catheter coordinates are used as the finally inferred catheter position. The catheter guide none-state judgment result derived from the spline interpolation is fixed relative to the one IVUS catheter location.

The detection results of the guiding catheter tip may not be reliable, so are inferred based on the multiple tip candidates. During the inference, a table of none-state indicators is maintained for all candidates, which are updated with the proceeding iteration. The validity check and removal of acts 32 and 34 are performed during each iteration. Since the tracked IVUS catheter has high reliability, all the candidates in a frame are in none-state status if the tracked IVUS catheter is in none-state status. Otherwise, as mentioned above, the guide tip none-state indicator for each candidate is updated, and the indicator of the selected candidate at each iteration is used as the none-state indicator of this frame.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for determining a first location of a first medical device in imaging, the method comprising:

obtaining a plurality of first candidate locations of a first medical device for each frame of a plurality of frames of medical data representing a patient, wherein at least one first candidate location of the plurality of first candidate locations does not represent the first medical device;

obtaining a plurality of second candidate locations of a second medical device for each frame of the plurality of the frames of the medical data;

selecting, with a processor, the first location of the first medical device in each frame of the plurality of frames from the plurality of first candidate locations for the respective frame, the selecting being iterative as a function of a probability function, the probability function being a function of the plurality of first candidate locations and the plurality of second candidate locations and distances between the plurality of first candidate location and the plurality of second candidate locations; and outputting an indication of the first location for at least one frame of the plurality of frames.

2. The method of claim 1 wherein selecting comprises identifying with the distances comprising geodesic distance along a curve.

3. The method of claim 1 further comprising obtaining the plurality of frames as angiography data with the first medical device comprising an intravascular ultrasound catheter, and the second medical device comprising a guide catheter.

4. The method of claim 3 wherein the plurality of first candidate locations are for a center of a transducer of the intravascular ultrasound catheter, and the plurality of second candidate locations are for a center of an end of the guide catheter.

5. The method of claim 1 wherein selecting comprises iteratively maximizing posterior probabilities of a Markov random chain, the Markov random chain being of the first locations in a sequence of the frames.

6. The method of claim 1 wherein selecting comprises optimizing the probability function, the probability function including differences between an inferred first location and a first candidate location of the plurality of first candidate locations nearest to the inferred first location, including differences between an inferred second location of the second medical device and a second candidate location of the plurality of second candidate locations nearest to the inferred second location, and including the distances between the plurality of first candidate locations and the plurality of second candidate locations.

7. The method of claim 6 wherein the differences between the inferred first location and the first candidate location and the differences between the inferred second location and the second candidate location comprise Euclidean distances.

8. The method of claim 1 wherein selecting comprises identifying with the probability function including probabilities for a first frame of the plurality of frames and probabilities for other frames of the plurality of frames, the probabilities for the other frames including predicted locations of the first location in the other frames, the probabilities being based on a Gaussian distribution.

9. The method of claim 1 further comprising:

checking validity of the plurality of first candidate locations, for each frame of the plurality of frames, as a function of location relative to a reference; and removing, from the selecting, any frames of the plurality of frames where the plurality of first candidate locations are not valid.

10. The method of claim 1 further comprising:

determining differences between the selected first locations of the plurality of frames; and interpolating the first location for any frame of the plurality of frames where the difference is greater than a threshold, the interpolation being from the first locations of other frames of the plurality of frames.

11. In a non-transitory computer readable storage medium having stored therein data representing instructions executable by a programmed processor for optimizing multiple candidates in medical device or feature tracking, the non-transitory computer readable storage medium comprising instructions for:

receiving a plurality of detected positions of a medical device or feature for each image frame of a plurality of image frames representing a patient, wherein at least one detected position of the plurality of detected positions does not represent the medical device or feature; and selecting one detected position of the plurality of detected positions in each image frame of the plurality of image frames, the selecting iteratively solving, for each image frame of the plurality of image frames, a probability function based on the plurality of detected positions in the image frame and a neighborhood of other image frames of the plurality of image frames.

12. The non-transitory computer readable storage medium of claim 11 wherein iteratively solving comprises solving as a function of a geodesic distance between the plurality of detected positions of the medical device and detected positions of another medical device, the geodesic distance being alone a curve.

13. The non-transitory computer readable storage medium of claim 11 wherein iteratively solving comprises solving the probability function, the probability function comprising probabilities for a first image frame of the plurality of image frames and probabilities for other image frames of the plurality of image frames, the probabilities for the other image frames including predicted positions of the selected one detected position in the other image frames, the probabilities being based on a Gaussian distribution.

14. The non-transitory computer readable storage medium of claim 11 further comprising:

checking validity of the plurality of detected positions, for each image frame of the plurality of image frames, as a function of position relative to a reference; and removing, from the selecting, any of image frames of the plurality of image frames where the plurality of detected positions are not valid.

15. The non-transitory computer readable storage medium of claim 11 further comprising:

determining differences between the selected ones of the plurality of detected positions of the plurality of image frames; and interpolating a device position for any image frames of the plurality of image frames where the difference is greater than a threshold, the interpolation being from the selected ones of the plurality of detected locations of other frames of the plurality of frames.

16. The non-transitory computer readable storage medium of claim 11 wherein receiving comprises receiving the plurality of image frames as fluoroscopy data with the medical device comprising an intravascular ultrasound catheter, and the plurality of detected positions are candidate locations of a center of the intravascular ultrasound catheter.

17. The non-transitory computer readable storage medium of claim 11 wherein iteratively solving comprises iteratively maximizing posterior probabilities of a Markov random chain.

18. The non-transitory computer readable storage medium of claim 11 wherein iteratively solving comprises optimizing the probability function, the probability function including differences between an inferred position and a detected position of the plurality of detected positions nearest to the inferred position, including differences between another inferred position of another medical device and another detected position of the other medical device nearest to the other inferred position, and including distances between the plurality of detected positions and the other detected positions, the differences comprising Euclidean distances and the distances comprising geodesic distances.

19. A system for optimizing multiple candidates in medical device tracking, the system comprising:

a memory configured to store data representing a region, at different times, of a patient and a catheter in the region;

a processor configured to calculate a location of the catheter in the region as represented by the data, the location calculated by inferring from a plurality of possible locations in the data at the different times in a Markov random chain, wherein at least one possible location of the plurality of possible locations does not represent the catheter, the inferring using iterated conditional modes to maximize posterior probabilities of the Markov random chain; and a display configured to display the location as calculated for each of the different times.

20. The system of claim 19 wherein the posterior probabilities are a function of a geodesic distance between the plurality of possible locations of the catheter and possible locations of a catheter guide.

* * * * *